United States Patent

Zarnack et al.

[11] Patent Number: 5,563,296
[45] Date of Patent: Oct. 8, 1996

[54] CONTINUOUS PROCESS FOR PREPARING AROMATIC AMINES

[75] Inventors: Uwe J. Zarnack; Fritz Pohl, both of Brunsbüttel; Dieter Grenner, Leverkusen; Hartmut Hetzel, Köln; Helmut Judat, Langenfeld, all of Germany

[73] Assignee: Bayer Aktiengesellschaft, Leverkusen, Germany

[21] Appl. No.: 268,407

[22] Filed: Jun. 30, 1994

[30] Foreign Application Priority Data

Jul. 15, 1993 [DE] Germany .............. 43 23 687.1

[51] Int. Cl.⁶ ................................. C07C 209/36
[52] U.S. Cl. ................. 564/422; 564/416; 564/420; 564/423
[58] Field of Search ............... 564/422, 420, 564/423, 416

[56] References Cited

U.S. PATENT DOCUMENTS

| | | | |
|---|---|---|---|
| 3,194,839 | 7/1965 | Robinson et al. | 260/575 |
| 3,356,728 | 12/1967 | Cimerol et al. | 260/580 |
| 3,356,729 | 12/1967 | Denton et al. | 260/580 |
| 3,431,085 | 3/1969 | Cimerol et al. | 23/288 |
| 3,546,296 | 12/1970 | Gobron et al. | 260/580 |
| 3,761,521 | 9/1973 | Alheritiere et al. | 260/580 |
| 3,781,373 | 12/1973 | Gobron et al. | 260/635 C |
| 3,882,048 | 5/1975 | Thelen et al. | 252/464 |
| 3,895,065 | 7/1975 | Alheritiere et al. | 260/583 R |
| 4,066,698 | 1/1978 | Clasen | 260/569 |
| 4,288,640 | 9/1981 | Schuster et al. | 568/855 |
| 4,792,626 | 12/1988 | Becher et al. | 564/422 |

FOREIGN PATENT DOCUMENTS

| | | |
|---|---|---|
| 1211757 | 9/1986 | Canada . |
| 263935 | 4/1988 | European Pat. Off. . |
| 2135154 | 2/1973 | Germany . |
| 229940 | 11/1985 | Germany . |
| 768111 | 2/1957 | United Kingdom . |
| 1017646 | 1/1966 | United Kingdom . |
| 1490313 | 12/1977 | United Kingdom . |

*Primary Examiner*—Brian M. Burn
*Attorney, Agent, or Firm*—Joseph C. Gil; Lyndanne M. Whalen

[57] ABSTRACT

Aromatic diamines and polyamines are produced by a continuous process for the catalytic hydrogenation of the corresponding dinitro and polynitro compounds at elevated temperature. Heat removed from the reaction mixture may be used to produce steam with an overpressure of ≧2 bar.

9 Claims, 1 Drawing Sheet

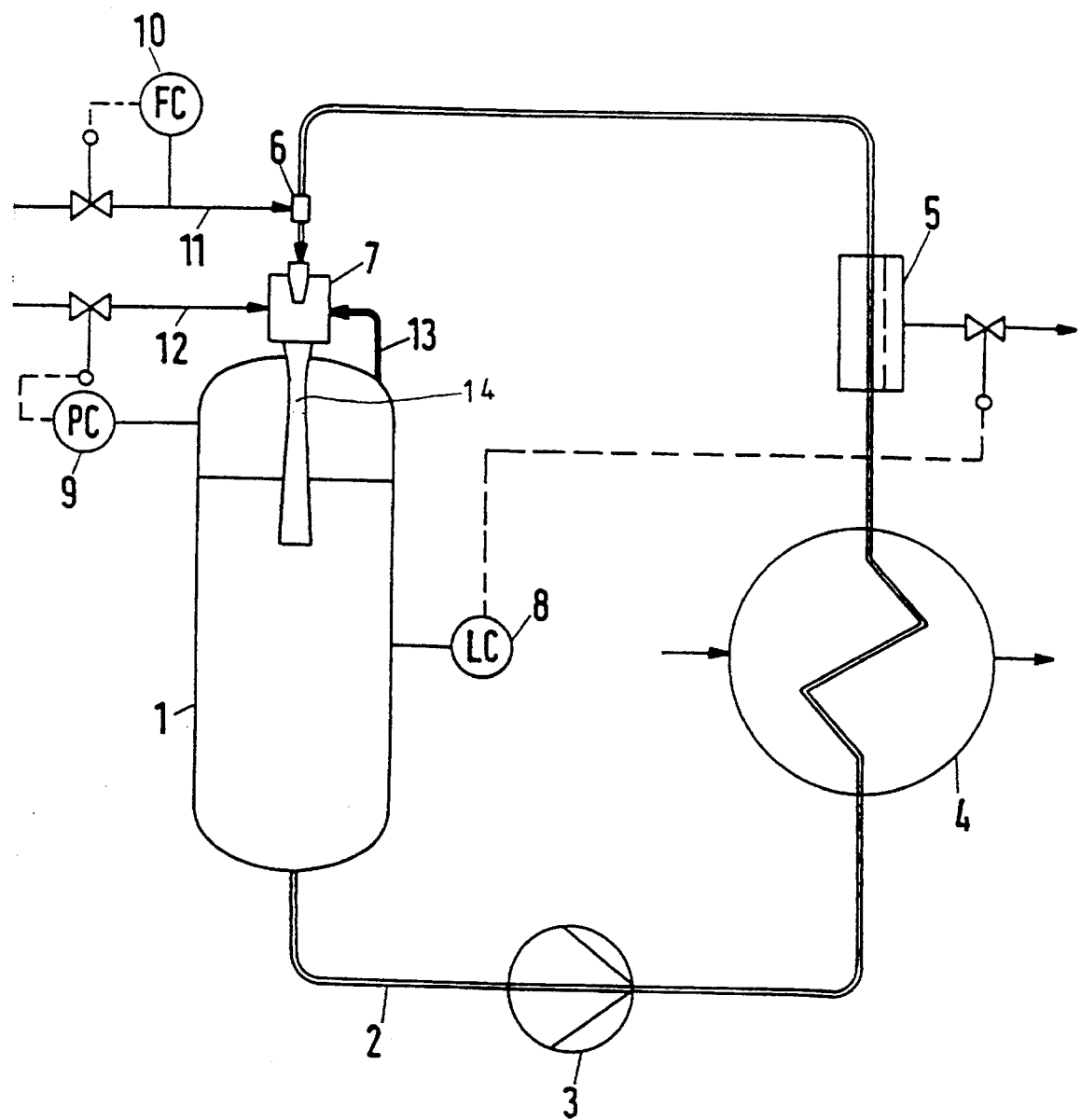

CONTINUOUS PROCESS FOR PREPARING AROMATIC AMINES

BACKGROUND OF THE INVENTION

The present invention relates to a continuous process for preparing aromatic di- and polyamines by catalytic hydrogenation of the corresponding di- and polynitro compounds.

A large number of processes for preparing aromatic amines by catalytic hydrogenation of nitro compounds is known. See, for example, U.S. Pat. Nos. 3,546,296; 3,781,373; 3,761,521; 3,895,065; 4,288,640; DE 2,135,154; U.S. Pat. No. 3,882,048; GB 1,490,313; GB 1,017,646; U.S. Pat. Nos. 3,356,728; 3,356,729; 3,431,085; 3,194,839 and GB 768,111.

A considerable amount of heat is released when aromatic polynitro compounds react with hydrogen. Attempts to make use of the heat of hydrogenation released during the preparation of aromatic polyamines by hydrogenation of the corresponding polynitro compound have been made. For example, the warm cooling water can be used to heat rooms or to warm product streams or even to evaporate low boiling solvents.

Generally, the large-scale hydrogenation of aromatic polynitro compounds is performed at the lowest possible temperature to reduce the risk of uncontrolled side reactions when hydrogenating aromatic polynitro compounds at elevated temperatures. Side reactions may lead to the formation of undesired by-products and thus to reduction in yield. Ring-hydrogenation, hydrogenolytic decomposition or the formation of macromolecular, tar-like products are examples of undesirable side reactions. Explosive side reactions may also take place. Such side reactions are caused by the strongly exothermic reaction of nitro-groups and their high rates of reaction at elevated temperatures.

To avoid these undesired side reactions as much as possible, the large-scale hydrogenation of aromatic polynitro compounds has generally been performed at temperatures such that the production of steam with an excess pressure of more than 2 bar would not take place.

Canadian Patent 1,211,757 describes a process for preparing aromatic dinmines by catalytic hydrogenation of the corresponding dinitro compounds with the simultaneous production of steam with an excess pressure of >1 bar. A bubble column provided with filled pipes is used as the reactor. The reactor is cooled by means of water which is converted into steam in the field pipes. A reaction suspension made up of an aromatic dinitro compound, the corresponding diamine, a hydrogenation catalyst, a saturated, aliphatic alcohol with 1 to 6 carbon atoms as solvent and water, is fed to the reactor with the hydrogen. The amount of reaction suspension supplied to the bubble column, and the pressure, temperature and amount of cooling water, are chosen so that the reaction temperature in the bubble column is between 140° and 250° C.

The disadvantage of the process described in Canadian Patent 1,211,757 is the use of a solvent. Although the solvent moderates the known problems of hydrogenation of polynitro compounds at elevated temperatures, it is not completely inert under the hydrogenation conditions. The solvent reacts to form undesired side products and reduces the yield of amine. Upon completion of the reaction, the solvent must be separated from the aromatic diamine and optionally worked up. Such treatments increase the cost of the process.

Attempts have been made to transfer the essential features of the process described in Canadian Patent 1,211,757 to a solvent-free catalytic hydrogenation of aromatic nitro compounds. EP 263,935 discloses a process in which stirred reactors are used to perform exothermic reactions. These reactors are cooled by means of water which is convened into steam with more than 1 bar excess pressure in field pipes. The ratio of cooling surface in the boiling tubes to the volume of the reaction space is 40 to 400 $m^2/m^3$. This high ratio has proven to be particularly effective for removal of the heat of reaction which is released. However, the process disclosed in EP 263,935 can only be Used to a limited extent for the catalytic hydrogenation of polynitro aromatic compounds because complete phase-mixing is not guaranteed. Due to inhomogeneities, intense and uncontrollable side reactions take place. These side reactions result in reduction in yield and coating of the cooling surfaces with resin-like compounds and/or a proportion of the catalyst.

SUMMARY OF THE INVENTION

It is an object of the present invention to provide a solvent-free process for producing aromatic amines by hydrogenation of aromatic nitro compounds.

It is also an object of the present invention to provide a process for producing aromatic amines by hydrogenation of aromatic nitro compounds which may be conducted at elevated temperatures without promoting side reactions.

It is another object of the present invention to provide a process for simultaneously producing aromatic amines and steam with an excess pressure of >2 bar.

These and other objects which will be apparent to those skilled in the art are accomplished by (1) introducing an aromatic dinitro or polynitro compound into a reactor containing a rapidly flowing mixture of amine, catalyst, water and hydrogen in a manner such that the nitro compound will be dispersed in the rapidly flowing mixture, (2) reacting the nitro compound with hydrogen to form the amine, and (3) continuously withdrawing amine-containing reaction mixture from the reactor. The mixing ratio is controlled during (1) so that the volume ratio of nitro compound introduced to mixture of amine, catalyst, water and hydrogen is within a specified range. The reactor is maintained at a pressure of from about 5 to about 100 bar and a temperature of from about 120° to about 220° C. The heat of the reaction may optionally be used to produce steam.

BRIEF DESCRIPTION OF THE DRAWING

The Figure illustrates one apparatus useful in the practice of the present invention.

DETAILED DESCRIPTION OF THE INVENTION

The present invention is directed to a continuous process for preparing aromatic di- and polyamines by catalytic hydrogenation of the corresponding aromatic di- and polynitro compounds. This process may be carried out in a loop-Venturi reactor with an ejector having a mixing chamber.

In the process of the present invention, the aromatic di- or polynitro compound is introduced, without a solvent, into a rapidly flowing mixture which is made up of aromatic diamine(s) or polyamine(s), a finely-divided suspended, solid hydrogenation catalyst, water and hydrogen. The nitro compound is introduced into the reactor in a manner such that the dinitro or polynitro compound(s) is very finely dispersed in the mixture. The ratio by volume of the rapidly flowing mixture present in the reactor to the di- or polynitro compound introduced into the reactor is maintained within the range of from about 50 to about 500. The ejector operates on the rapidly flowing mixture in such a way that an energy of 4 to 40 kW/t of di- or polynitro compound introduced is dissipated in the ejector mixing chamber. The ratio of the volume flow of hydrogen admitted to the rapidly flowing, optionally recirculated, mixture volume is maintained at from 0.1 to 7. The hydrogen required is drawn into the gas chamber of the reactor and the hydrogen consumed during reaction may be supplied at any point in the system. Reaction mixture is continuously withdrawn from the system. A pressure of from about 5 to about 100 bar and an operating temperature of from about 120° to about 220° C. are maintained in the reactor. The heat of reaction may optionally be used to produce steam.

A pressure of from about 10 to about 50 bar and an operating temperature of from about 150° to about 200° C. are preferably maintained in the reactor.

The product aromatic diamine or polyamine may be withdrawn from the system at any point. Withdrawal is preferably performed on the pressure side of a recirculating pump. In a particularly preferred embodiment of the present invention, the product diamine is withdrawn on the pressure side of a recirculating pump via a filter unit.

The product diamine or polyamine may also be withdrawn from the reactor itself. Where the product is withdrawn from the reactor itself, it is preferred that the product be recovered via a settling zone. Any catalyst present in the product may be separated from the product (e.g., by sedimentation in a settling zone) and then returned to the system.

Preferably the product is removed while retaining the catalyst in the system.

In the process of the present invention, the aromatic di- or polynitro compound may be used in the pure form, as a mixture with the corresponding di- or polyamine or as a mixture with the corresponding di or polyamine and water.

The aromatic di- or polynitro compound is introduced to the flowing mixture present in the reactor in such a way that the nitro compound is very finely dispersed therein. This may be accomplished by means of a perforated nozzle or via some other suitable device.

The nitro compound is preferably introduced into the ejector (such as that identified by the number 7 in the Figure), most preferably into the ejector mixing chamber.

Examples of preferred aromatic nitro compounds which may be used to produce amines in accordance with the present invention include: 1,3-dinitrobenzene, 2,4-dinitrotoluene, 2,6-dinitrotoluene and industrial mixtures of dinitrotoluenes which are made up predominantly of the 2,4- and 2,6-isomers of dinitrotoluene.

2,4-dinitrotoluene and industrial mixtures of dinitrotoluene in which up to 35 wt.% of 2,6-dinitrotoluene, based on the total mixture, is present are more preferably used as the aromatic nitro compounds to be hydrogenated in accordance with the present invention. These industrial mixtures may also contain small amounts, (i.e. up to a maximum of 6 wt. %, based on the total mixture) of 2,3-, 2,5- or 3,4-dinitrotoluene.

Any of the hydrogenation catalysts known to be useful for hydrogenating aromatic nitro compounds may be used in the process of the present invention. Examples of suitable catalysts include the metals of the 8th subgroup in the Periodic System of Elements. These may be applied to a supporting material such as an oxide of magnesium, aluminum and/or silicon. Raney iron, cobalt and/or nickel, particularly Raney nickel, are preferably used.

The catalyst is used in a finely dispersed state. The catalyst is finely divided and suspended in the reaction suspension. Maintenance of this suspension while carrying out the process of the present invention is ensured by the circulation through, for example, the ejector nozzle.

When carrying out the process of the present invention, particular care must be taken that:

(1) circulation of the reaction mixture takes place in such a way that the ratio by volume of the mixture (containing amine, catalyst, water and hydrogen) to the nitro compound introduced is 50 to 500, preferably 200 to 300;

(2) the energy dissipated at the ejector nozzle is 4 to 40 kW/t of nitro compound introduced;

(3) the injector nozzle draws in automatically, i.e. that hydrogen gas collecting in the upper part of the reactor is automatically re-mixed into the reaction mixture by the energy of the recirculated mixture;

(4) the operating pressure of the system is maintained by introducing fresh hydrogen from outside of the reactor; and (5) the ratio by volume of the hydrogen stream admitted to the mixture being circulated is 0.1 to 7.

The intense mixing of all the components at low substrate concentrations and with the avoidance of contact times solely between the substrate and the catalyst is achieved by the introduction of the aromatic nitro component (preferably in the mixing chamber of the ejector) in conjunction with the remaining process parameters.

This means that a solvent-free, catalytic hydrogenation of di- and polynitro aromatic compounds simultaneously with the production of steam at an overpressure of more than 2 bars with heat removed from the hydrogenation reaction is possible at elevated temperatures. Side reactions do not occur or occur to only a small extent.

The process of the present invention is preferably performed in apparatus like that described in Chem. Eng. Sc., vol. 47, no. 13/14, p. 3557–3564 (1992) or in VT "Verfahrenstechnik" 15 (1981) no. 10, p. 738–749. Any other apparatus having the essential features of these apparatus may also be used.

An example of an apparatus useful for carrying out the process of the present invention is shown schematically in the Figure. The numbers in the Figure have the following meaning:

(1) the reactor (2) piping for recirculating the reaction mixture (3) pump for recirculating the reaction mixture (4) heat-exchanger to cool the recirculated reaction mixture (5) filter unit to withdraw the aromatic amine and retain the catalyst (6) feed mechanism for the aromatic nitro compound (7) ejector to admit hydrogen to the reaction mixture (8) regulator (9) pressure control (maintenance of pressure)

(10) regulator (controls amount of aromatic nitro compound fed to supply line)

(11) feed line for aromatic nitro compound

(12) feed line for hydrogen

(13) hydrogen transfer line

The process of the present invention may be carried out in the apparatus illustrated in the Figure. An example of a specific process carried out in the illustrated apparatus will be described in more detail below.

In the process of the present invention, the hydrogenation of, for instance, dinitrotoluene (DNT), may be carried out in a loop reactor with an ejector. The reaction which is preferably performed at a pressure of 25 bar and a temperature of 185° C., is strongly exothermic. The heat released during the reaction heats the reaction mixture considerably. Because selectivity deteriorates with increasing temperature, it is advantageous to restrict the temperature increase of the reaction mixture to 10° C. or less. This can be achieved in a simple manner by adjusting the mass flow rate of recirculated mixture to the amount of heat being released and the temperature increase which can be tolerated.

For example, 2,756,000 kcal/h are released during the hydrogenation of 2000 kg/h of dinitrotoluene. The permitted maximum temperature of 185°+10°=195° C. will not be exceeded if the mass flow rate of recirculated reaction mixture is at least 372 t/h. If the amount of DNT introduced is 1500 I/h, a volume ratio of amount of mixture to amount of DNT of 372 000:1500=248:1 is produced. When using catalysts which are less temperature-sensitive, larger temperature increases may be tolerated and the mixture may be pumped around at a slower rate.

The reaction could be easily carried out if the recirculated volume flow of hydrogen required to convert the DNT were present in the dissolved form. Unfortunately, the reaction mixture can only dissolve a maximum of 0.132 g/l of hydrogen under the given conditions (25 bar, 185° C.). A volume flow of 372 m³/h which contains only 49.1 kg of hydrogen is therefore the maximum. Since 132 kg/h of hydrogen are required for complete conversion of 2000 kg/h of DNT, the dissolved hydrogen constitutes only 37.2% of the total amount of hydrogen required. The missing amount of 82.9 kg/h of hydrogen must therefore be supplied at the site of reaction. Therefore, the ejector 7 is operated in such a way that the material transfer conditions required for the introduction of the missing amount of hydrogen to take place are provided. Where the reaction is carried out at 25 bar and 185° C. to 195° C., the ejector 7 must admit at least 100 m³/h of hydrogen of which 62.8% must dissolve in the mixing pipe and the remainder in the subsequent container. The ratio of admitted volume flow of gas to recirculated volume flow of reaction mixture is thus at least 100:372= 0.269. Since the amount of gas to be dispersed is relatively small, the total amount of hydrogen of 132 kg/h can easily be dissolved in the ejector mixing pipe alone. In order to be certain that there is no depletion of dissolved hydrogen in the recirculated reaction mixture, it is expedient to admit an amount of hydrogen which is larger than the minimum required amount of 100 m³/h.

Even if the system is operated with a recirculated rate of flow of 372 m³/h and a 3-fold amount of $H_2$ (that is, 300 m³/h is admitted), the conditions in the ejector mixing pipe can be chosen so that 132 kg/h of hydrogen are completely dissolved in this section of the reaction path. This complete dissolution may be achieved, for example, by adjusting the volume-specific introduction of energy in the ejector. The intensity of mixing can be varied over wide limits by the choice of nozzle geometry and adjustment of the amount of energy introduced into the ejector to satisfy particular requirements. For example, if 37.3 kW of power are introduced to a recirculated stream of 372 m³/h with a nozzle of 70 mm diameter, the volume-specific introduction of energy will be from about 2.9 to about 6.8 kW/l, depending on the size of the mixing chamber. Related to a mass of 2 t of DNT being hydrogenated per hour, 18.65 kW/t of DNT introduced is the volume-specific amount of energy which should be fed to the ejector to achieve the desired dispersion of hydrogen being introduced to the reactor.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A continuous process for producing aromatic diamines and/or polyamines comprising
   1) introducing (a) an aromatic dinitro and/or polynitro compound, without a solvent, into a reactor maintained at a pressure of from about 5 to about 100 bar and a temperature of from about 120° to about 220° C. in which (b) a rapidly flowing mixture of
      (i) aromatic diamine and/or polyamine,
      (ii) finely-divided, suspended, dispersed hydrogenation catalyst,
      (iii) water,
   and
      (iv) hydrogen is present in a manner such that
         (A) the aromatic dinitro and/or polynitro compound is very finely dispersed in the mixture,
         (B) the ratio by volume of mixture (b) to nitro compound (a) introduced is 50 to 500,
         (c) 4 to 40 kW/t of nitro compound (a) introduced is dissipated in the mixing chamber of the ejector,
   2) reacting the nitro compound (a) with hydrogen to form a diamine and/or polyamine,
   3) continuously withdrawing amine-containing mixture from the reactor,
   4) removing hydrogen from the gas chamber of the reactor and introducing hydrogen to replace the quantity of hydrogen consumed in 2) at any desired point in the system, so that the volume flow of hydrogen in relation to the circulated volume of mixture is from 0.1 to 7
   5) using heat generated in the reactor during 2) to produce steam.

2. The process of claim 1 in which the reactor is maintained at a pressure of from about 10 to about 50 bar.

3. The process of claim 2 in which the temperature of the reactor is maintained at 150° to 200° C.

4. The process of claim 1 in which the temperature of the reactor is maintained at 150° to 200° C.

5. The process of claim 1 in which the product is removed while retaining the catalyst in the system.

6. The process of claim 1 in which the nitro compound (a) is selected from the nitro compound in pure form, a mixture of the nitro compound with the corresponding diamine or polyamine or a mixture of the nitro compound with the corresponding diamine or polyamine and water.

7. The process of claim 1 in which nitro compound (a) is selected from 2,4-dinitrotoluene and mixtures of 2,4-dinitrotoluene with 2,6-dinitrotoluene.

8. The process of claim 1 in which the process is carried out in a loop-Venturi reactor with an ejector having a mixing chamber.

9. The process of claim 8 in which the ejector operates on mixture (b) in such a way that 4 to 40 kW per metric ton of nitro compound (a) is dissipated in the ejector mixing chamber.

* * * * *